US005941867A

United States Patent [19]

Kao

[11] Patent Number: 5,941,867

[45] Date of Patent: Aug. 24, 1999

[54] FORMULATION OF PHARMACEUTICAL SOLUTIONS IN FREE FALL

[76] Inventor: Ti Kao, P.O. Box 740014, Rego Park, N.Y. 11374-0014

[21] Appl. No.: 09/075,145

[22] Filed: May 8, 1998

Related U.S. Application Data

[63] Continuation-in-part of application No. 08/892,571, Jul. 15, 1997.

[51] Int. Cl.[6] ........ A61B 19/00

[52] U.S. Cl. ........ 604/416; 604/408; 604/410; 604/403; 604/82; 604/85; 604/87; 604/92

[58] Field of Search ........ 604/82, 83, 84, 604/85, 87, 89, 403, 408, 405, 406, 410, 416, 903, 500; 221/636, 91, 2

[56] References Cited

U.S. PATENT DOCUMENTS

| | | | |
|---|---|---|---|
| 3,502,244 | 3/1970 | Irvin | 221/63 |
| 4,128,188 | 12/1978 | White | 221/91 |
| 4,175,558 | 11/1979 | Hess, III et al. | 128/214 |
| 4,340,152 | 7/1982 | Ekholm, Jr. | 222/1 |
| 4,540,403 | 9/1985 | Theeuwes | 604/85 |
| 4,785,969 | 11/1988 | McLaughlin | 221/2 |
| 4,863,454 | 9/1989 | LaBove | 604/416 |
| 4,906,103 | 3/1990 | Kao | 366/130 |
| 4,980,292 | 12/1990 | Elbert et al. | 435/289 |
| 5,014,875 | 5/1991 | McLaughlin et al. | 221/2 |
| 5,181,189 | 1/1993 | Hafner | 368/10 |
| 5,190,185 | 3/1993 | Blechl | 221/1 |
| 5,196,001 | 3/1993 | Kao | 604/416 |
| 5,208,762 | 5/1993 | Charhut et al. | 364/478 |
| 5,263,929 | 11/1993 | Falcone et al. | 604/89 |
| 5,278,149 | 1/1994 | Provost et al. | 514/23 |
| 5,329,459 | 7/1994 | Kaufman et al. | 364/479 |
| 5,348,061 | 9/1994 | Riley et al. | 141/104 |
| 5,377,864 | 1/1995 | Blechl et al. | 221/2 |
| 5,460,294 | 10/1995 | Williams | 221/2 |
| 5,494,196 | 2/1996 | Tyner | 222/147 |
| 5,502,944 | 4/1996 | Kraft et al. | 53/55 |
| 5,511,594 | 4/1996 | Brennan et al. | 141/98 |

*Primary Examiner*—Ronald Stright, Jr.
*Assistant Examiner*—N. Kent Gring
*Attorney, Agent, or Firm*—Lathrop & Clark LLP

[57] ABSTRACT

Sterile solutions containing pharmaceuticals suitable for use in low and micro-gravity environments are prepared with unit dose pharmaceutical dispensers having a pre-measured quantity of medicament. A compressed air reservoir may be activated to rupture the dispenser and positively expel the unit dose into solution. This can be accomplished by inverting a bag containing the pharmaceutical or by operation of a piston which pushes all the pharmaceutical from the dispenser. A robot either places the pharmaceutical dispensers inside a mixing chamber or connects the dispensers to the mixing chamber, which comprises a flexible bag expandable to receive sterile water and pharmaceuticals. The mixing chamber may collapse under cabin pressure to drive prepared solutions from the chamber through a sterilization filter into an intravenous bag or dispensing unit. Sterile water or saline solution is contained in pre-measured dispensing units employing similar principles to the pharmaceutical dispensers, with a positive expulsion bladder similar to that employed in a zero gravity fuel tank. A robotic, manually activated, or squib-activated valve injects a predetermined quantity of air into the solution container, where the air expands again a membrane or the surface of the fluid, causing it to flow through a check valve into the mixing container. The mixing container is mounted on a vibrating arm driven by a rotary electric motor or a piezoelectric motor which causes agitation until the mixture is uniformly mixed. A sensor may monitor the progress of dissolution of the pharmaceutical suspension through observing optical index of refraction.

11 Claims, 5 Drawing Sheets

FORMULATION OF PHARMACEUTICAL SOLUTIONS IN FREE FALL

RELATED APPLICATIONS

This application is a Continuation-In-Part of U.S. application Ser. No. 08/892,571, filed Jul. 15, 1997 now pending, the disclosure of which is incorporated by reference herein.

FIELD OF THE INVENTION

The present invention relates to devices and methods for the preparation of pharmaceutical solutions in particular, and in particular to devices for preparing such solutions by remote control.

BACKGROUND OF THE INVENTION

Typically, bags of solutions for intravenous injection of patients are prepared manually by pharmacists or pharmacist's aides. Each solution must be tailored to the particular needs of the patient with respect to composition, quantity and type of medicament, and pH level. Variations from required levels can have deleterious, even fatal, consequences for the patient. Pharmacists and their assistants are highly trained and conscientious professionals. Nonetheless, under the pressures of time and environment, these professionals can make errors. In addition, the need to keep the final preparation sterile requires costly and time-consuming measures on the part of those who prepare the solutions.

Heat sterilization of solutions for intravenous injection, for example as part of a total parenteral nutrition system can lead to carmelization of the injectable sugars, which can have enormously negative consequences for the health of the patient.

In my prior U.S. Pat. No. 4,906,103 I disclosed a system for the cold sterilization of solutions which completely avoids the hazards of heat sterilization. In my prior U.S. Pat. No. 5,196,001 I disclosed a preparation assembly and unit dose medicament containers for use in a cold sterilization system which permitted controlled pre-preparation dosing of medicaments.

Since the introduction of Total Parenteral Nutrition (TPN), manufacturers have not been able to overcome the chemical incompatibility of the glucose solution with the amino acid solution, due to the Maillard reaction. Hence, the glucose and amino acid solutions have had to be bottled separated at the manufacturer, and then prepared as the TPN solution in the hospital's Intravenous Admixture Room at substantial cost to the patient.

The conventional heat sterilization process has a number of drawbacks which are overcome by the use of cool sterilization. Among the problems with heat sterilization are:

1. Inverted sugar and dextrose injectibles have a neutral pH, however heat sterilization makes these injectibles acidic with a carmelization of the sugar and the dextrose.

2. When the solution is heated in the container, be it glass or plastic, the container material goes into solution with the heated liquids and reacts with the chemical solution to form particulate matter. Particulate matter is undesirable in an injected substance.

3. Heat sterilization produces 5-hydroxymethylfurfural and related substances which are highly acidic and poisonous degraded impurities from sugar.

By using cool sterilization, the upper and lower limitation of percentage of sugars can be narrowed down into a controllable range. Because the 5-hydroxymethylfurfural and hydroxymethylfurfural from fructose are not produced in the cool sterilization process, it is expected that it will be possible to maintain the purity of the sugars in a range better than the U.S. Pharmacopeia's range for heat sterilization of 95 percent to 105 percent.

Great strides have been made in automatic dispensing of solid pills and powders by way of computer controlled robotic assemblies. With greater attention to costs at all levels of the health care system, efforts have been made to limit the direct intervention of doctors and pharmacists in dispensing of medications, while at the same time maintaining adequate control by these professionals. Solid pills and capsules are by their nature suited to dispensing in unit doses, but the remotely operated drawers and dispensers which are adequate for pills are not effective for the preparation of individualized injectable solutions. Furthermore, robotic devices for dispensing liquids from a storage vessel of liquid present serious concerns in the preparation of solutions for administration to humans. Typically an aliquot of liquid would be dispensed by a micropump. Yet pumps are subject to malfunctions, and great care needs to be taken to quality check whether the desired quantity of liquid has actually been dispensed. In any event, no physical record remains to verify the amount and type of liquid dispensed. What is needed is a consistent and effective apparatus for preparing and dispensing liquid medicament solutions.

With the expanded exploration and commercialization of remote regions, both on earth and in space, before long many workers and explorers will be stationed at distant outposts far from the aid or intervention of licensed pharmacists and physicians. Nevertheless, these pioneers are placed at their posts at great cost, and represent a tremendous investment in training, capital, and transportation. Should such an isolated worker become ill or injured, the finest health care and medical intervention will be called for. What is needed is a system for providing the intravenous injectable solutions which can be controlled by skilled professions far removed from the site of injection.

SUMMARY OF THE INVENTION

The invention comprises a method and apparatus for mixing and preparing sterile solutions containing pharmaceuticals suitable for use in low and micro gravity environments. The apparatus employs unit dose pharmaceutical dispensers. The dispensers incorporate a pre-measured quantity of a pharmaceutical liquid or suspension. The dispensers incorporate a compressed air reservoir. Activation of the dispensers causes the compressed air to rupture the dispenser and positively expel the unit dose of pharmaceutical. This can be accomplished by inverting a bag containing the pharmaceutical or by operation of a piston which pushes all the pharmaceutical from the dispensing.

A robot places the pharmaceutical dispensers either inside a mixing chamber or connects the dispensers to the mixing chamber. The mixing chamber comprises a flexible bag which can expand to receive sterile water and pharmaceuticals. The mixing chamber can also collapse under cabin pressure to drive prepared solutions from the chamber through a sterilization filter and into an intravenous bag or dispensing unit.

Sterile water or saline solution is contained in pre-measured dispensing units employing similar principles to the pharmaceutical dispensers. Here a positive expulsion bladder similar to that employed in a zero gravity fuel tank may be employed. Devices also used in zero gravity fuel tanks, employing surface tension to separate fluids from air may also be employed. A robotic, manually activated, or squib activated valve injects a pre-determined quantity of air into the solution container, where the air expands again a membrane or the surface of the fluid, causing it to flow through a check valve into the mixing container.

The mixing container is mounted on a vibrating arm driven by a rotary electric motor or a piezoelectric motor which causes agitation until the mixture is uniformly mixed.

The mixing container incorporates transparent portions on which a turbidity sensor can be mounted to monitor the progress of dissolution of the pharmaceutical suspension. A similar sensor monitoring optical index of refraction can be used to determine complete mixing of dissolved pharmaceuticals, as it will be observed when the solution is evenly mixed that the index of refraction of the liquid contained in the mixing container will be uniform.

An intravenous administration container for bags is connected to a rapid filtration and sterilization unit which in turn is connected to the mixing chamber. A vacuum jacket is placed around the intravenous bags and the reduced pressure on the bags draws the solutions in the mixing chamber into the administration bag through the sterilization filter.

The unit dose containers remain within or attached to the mixing container serving as a positive record of what pharmaceuticals have been added to the intravenous solution.

The apparatus of this invention employs robotic manipulation of three-part plastic preparation assemblies to automatically produce IV solutions which conform to the pharmacist's input specifications. The assemblies are stored in a magazine, and are extracted automatically one by one for preparation of individual prescriptions. A supply bag is prefilled with U.S.P. water and is connected through a valve to a transparent plastic mixing bag. Unit dose holders containing various medicaments and pH adjusting chemistries are dispensed into the mixing bag through an inlet. The unit dose holders are broken open by manipulation of the bag, and the U.S.P. water is introduced into the bag through the inlet. The contents of the unit dose holders and the water may be mixed within the mixing bag by rotation of a magnetic mixing bar. The mixing bag is connected by a second valve through a filter to an administration bag. Negative pressure is applied to the administration bag to draw the solution through the filter. The administration bag is then heat sealed and severed from the filter for delivery to the patient. For ophthalmic solutions, a plurality of precapped containers are formed on the administration bag, and liquid from the administration bag is drawn into the individual ophthalmic solution containers, which are then heat sealed and severed from the administration bag.

The assembly of this invention is well suited to remote preparation of solutions, or to automated preparation of solutions, both under the supervision of a pharmacist. Furthermore, the exhausted mixing bag for each prepared solution may be stored, or an image of it may be stored, for later analysis of a particular solution should questions arise about its content after it has been administered to a patient. The assembly may be used for telerobotic preparation of solutions aboard spacecraft, where a licensed pharmacist will usually not be on site.

It is an object of the present invention to provide an apparatus for formulating solutions for intravenous injections without significant human intervention.

It is an additional object of the present invention to provide an apparatus for automatically and reliably preparing intravenous solutions.

It is another object of the present invention to provide an injectable solution system which displays visual markers to validate the prescribed contents of the solution.

It is a further object of the present invention to provide an apparatus for preparing human injectable solutions which may be operated in space by an earthbound pharmacist.

It is a still further object of the present invention to provide an apparatus for automatically preparing solutions for ophthalmic application.

Further objects, features and advantages of the invention will be apparent from the following detailed description when taken in conjunction with the accompanying drawings.

DESCRIPTION OF THE PREFERRED EMBODIMENTS

Figure 1:
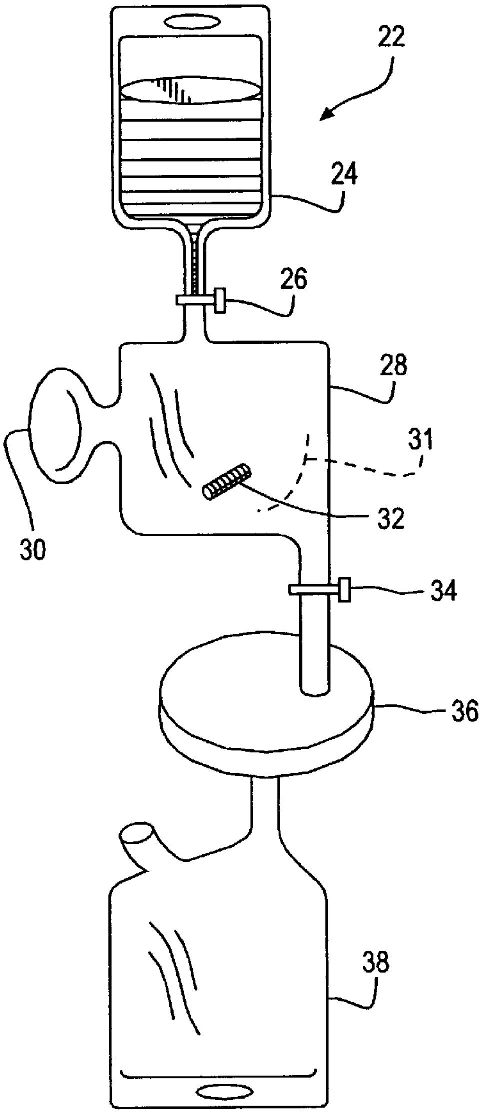
FIG. 1 is a schematic view of a preparation assembly for use within the robotic apparatus of this invention.

Referring more particularly to FIGS. 1–9, wherein like numbers refer to similar parts, a robotic solution preparation apparatus 20 of this invention with general application for automatic preparation of intravenous or ophthalmic solutions either under close or remote supervision by a pharmacist will be discussed first, with a specific embodiment for use in regions of so-called "zero-gravity" (more accurately "free fall") will be discussed hereafter. The apparatus 20 employs preformed preparation assemblies 22 which are stored in a magazine for immediate access by the mechanism 20. Each preparation assembly has three connected bags in which the solution is prepared and contained. A transparent plastic supply bag 24, as shown in FIG. 1, is prefilled and stored with U.S.P. water. The supply bag 24 is connected through a first valve 26 to a mixing bag 28. The mixing bag is also transparent plastic and has an inlet 30 through which unit dose containers are introduced into a mixing chamber 31. A magnetic mixing bar 32 is disposed within the mixing bag, or may be added in the mixing step. The mixing bag 28 is connected by a second valve 34 through a filter 36 to an administration bag 38.

Figure 2:
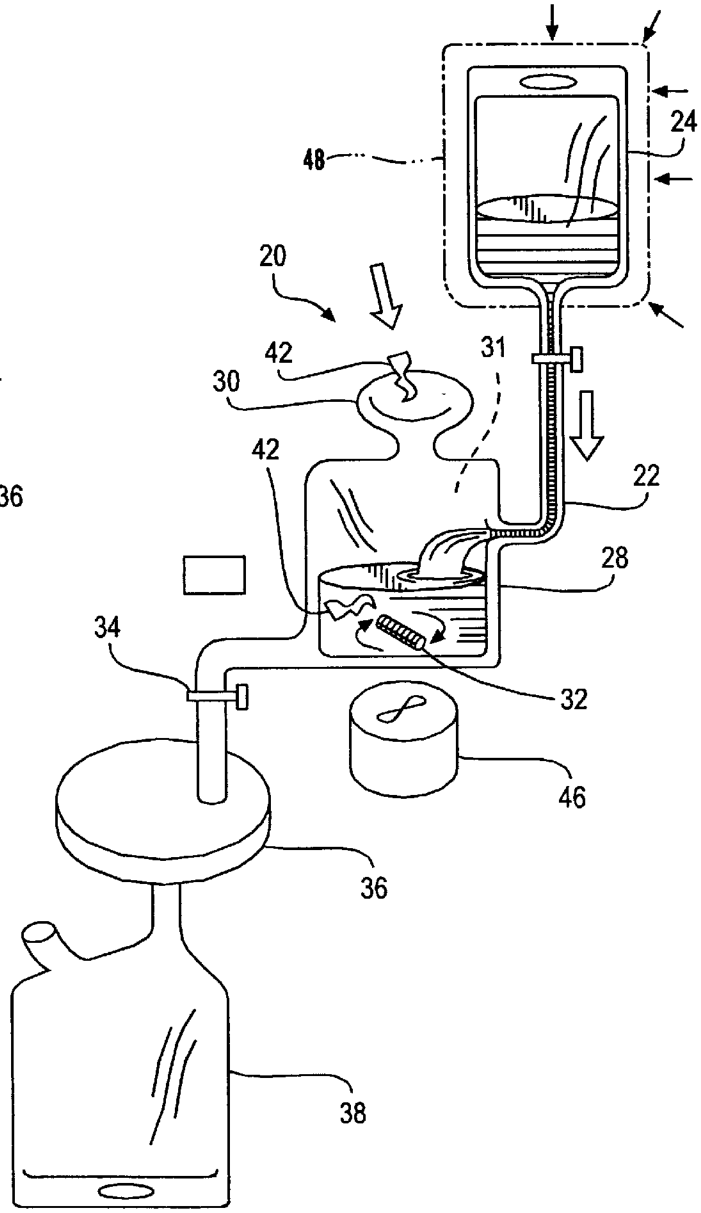
FIG. 2 is a schematic view of the assembly of FIG. 1 engaged within the robotic apparatus and showing the addition of prepared unit doses of medicaments and chemicals.

When it is desired to prepare a solution for intravenous administration, the pharmacist enters the required prescription into the computer controller. The controller then causes a preparation assembly 22 to be accessed from the magazine. In a preferred embodiment the controller will control the mechanisms associated with the apparatus without human intervention until the completion of the final container of solution for administration to a patient. The apparatus has a means for supporting and advancing the assembly 22 from the magazine which may be any conventional conveyor apparatus. The preparation assembly 22 is advanced so as to enclose the supply bag 24 in a positive pressure chamber 40, as shown in FIG. 2. While the supply bag 24 is subjected to positive pressure to force U.S.P. water from the supply bag 24 through the first valve 26, the mixing bag 28 is positioned with its inlet 30 opening upwardly such that unit dose holders 42 may be deposited into the mixing chamber 31. Because the unit dose holders are solid, easily manipulated objects, unit dose holders for a variety of medicaments may be stored in an automatically accessible rack or magazine for selection by the apparatus 20. When the mixing bag inlet 30 is in position, the controller directs that the proper number and type of unit dose holder 42 are introduced into the mixing chamber 31. The unit dose holders 42 contain premeasured quantities of medicaments and pH adjusting chemistries.

As the unit dose holders are introduced into the mixing chamber 31, they are broken to allow the powders or concentrated liquids contained therein to escape and mingle with the U.S.P. water contained in the mixing chamber 31. The unit dose holders 42 may be broken by several means. For example, the dose holders my be broken by a mechanism which ruptures them as they are dropped into the mixing bag so both the medicament contents and the empty holders enter the mixing bag, or they may be broken by a mechanism which massages the mixing bag after they have been introduced. In any event, both the contents of the unit dose holder and the unit dose holder itself are delivered into the mixing bag. The contents are mixed by a magnetic bar stirrer 46 positioned beneath the mixing bar 32 which causes the mixing bar to rotate and to thereby thoroughly mix the contents. The unit dose holders 42 may be of the type disclosed in my U.S. Pat. No. 4,906,103 and U.S. Pat. No. 5,196,001, the disclosures of which are incorporated by reference herein, or of the type shown in FIGS. 6–8. An electric eye 44 is positioned to detect the level of the contents within the mixing chamber 31. When the proper level is reached, the pressure on the supply bag 24 is halted.

Figure 3:
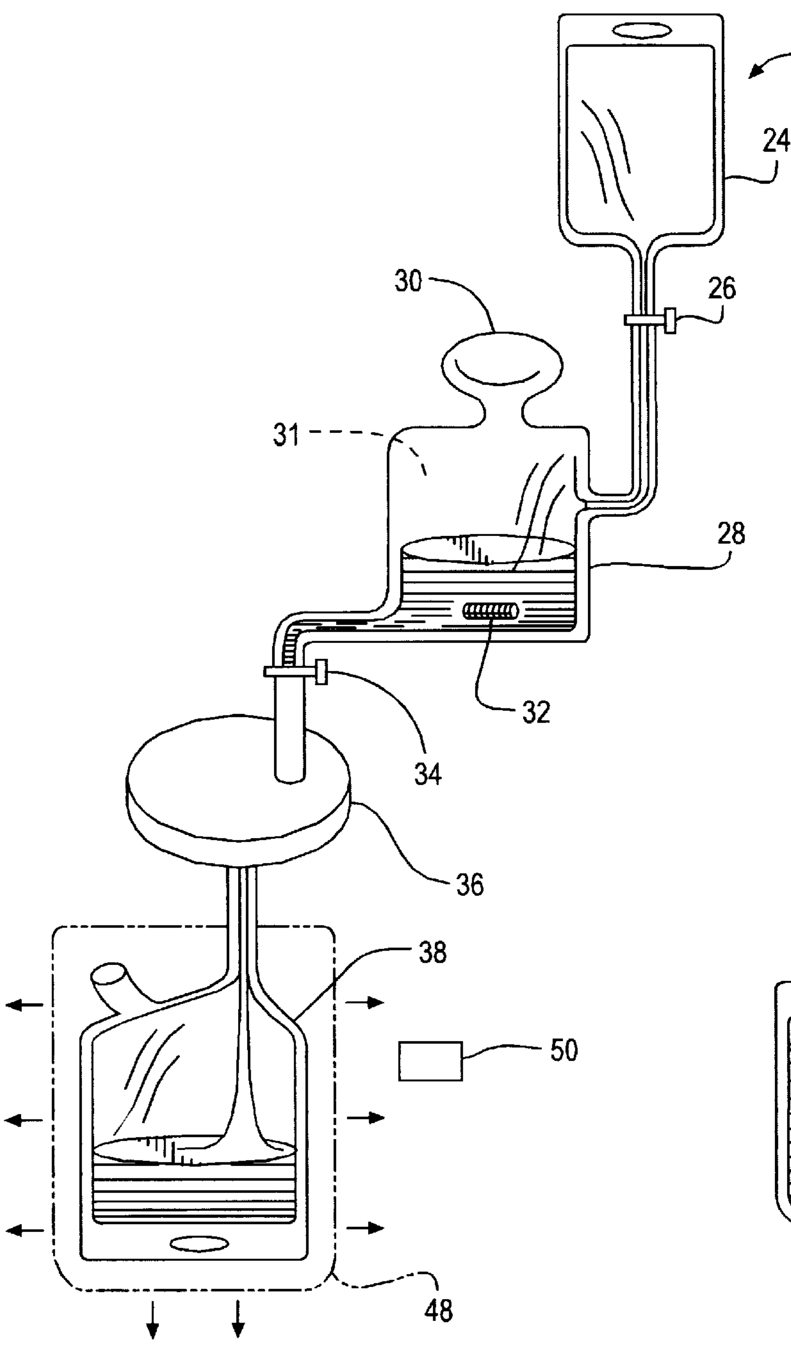
FIG. 3 is a schematic view of the assembly of FIG. 2 within the robotic apparatus with the administration bag being subjected to reverse pressure to draw the solution through a filter.
Figure 4:
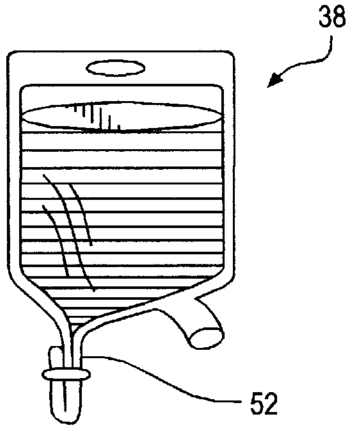
FIG. 4 is a schematic view of the final dispensed administration bag containing a sterile solution ready for patient administration.

As shown in FIG. 3, after mixing, the second valve 34 is opened and the administration bag is placed in a negative pressure chamber 48, where negative pressure is drawn to cause the liquid to pass through the filter 36 into the administration bag. An electric eye 50 is positioned to determine the level and specific density of the liquid within the administration bag 38, and to halt the application of negative pressure when desired levels are reached. The filter 36 sterilizes the solution without requiring it to be subjected to elevated temperatures.

The apparatus 20 then severs the administration bag 38 from the preparation assembly 22, and seals the end 52 such as by heat sealing. The administration bag 38 is then dispensed from the apparatus 20 for delivery to the patient and intravenous administration. It should be noted that the apparatus 20 may be constructed using conventional conveyance mechanisms, and that the assemblies 22 may be constructed with protruding engagement openings or position markers to assist in precise placement and manipulation of the assemblies by robotic elements.

Figure 6:
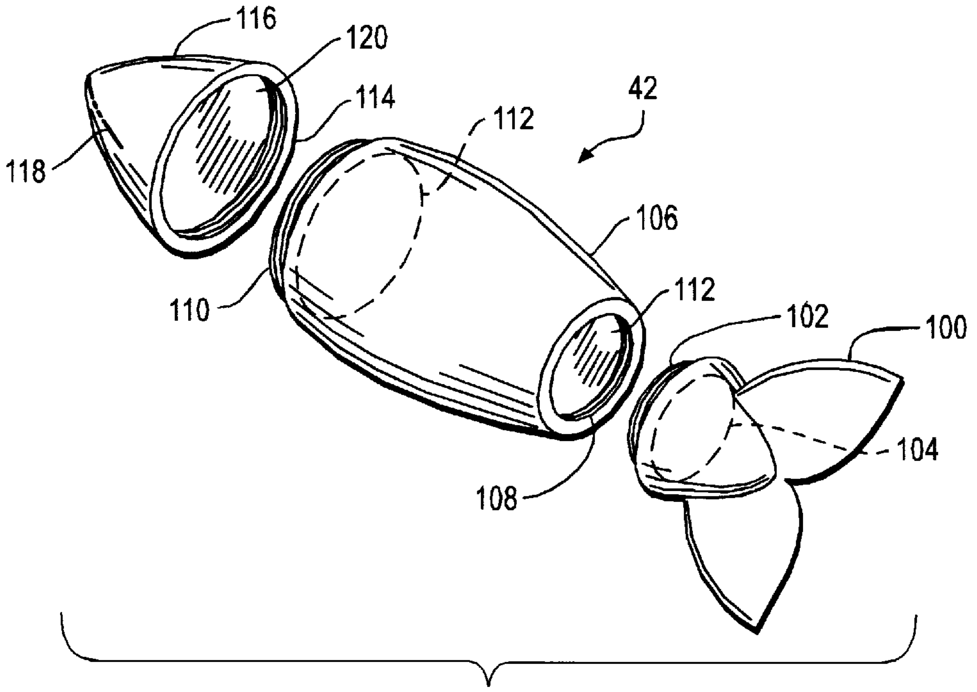
FIG. 6 is an exploded isometric view of a unit dose holder for use within the assembly of FIG. 1.
Figure 7:
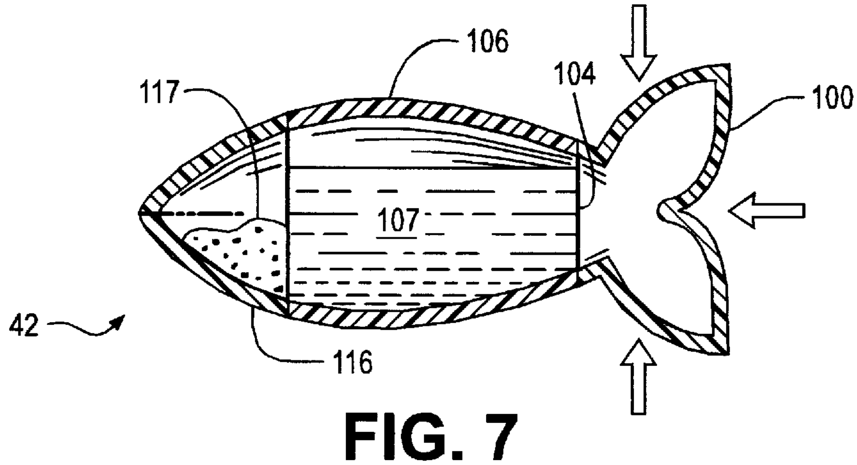
FIG. 7 is a cross-sectional view of the unit dose holder of FIG. 6, showing the location of pressure application.
Figure 8:
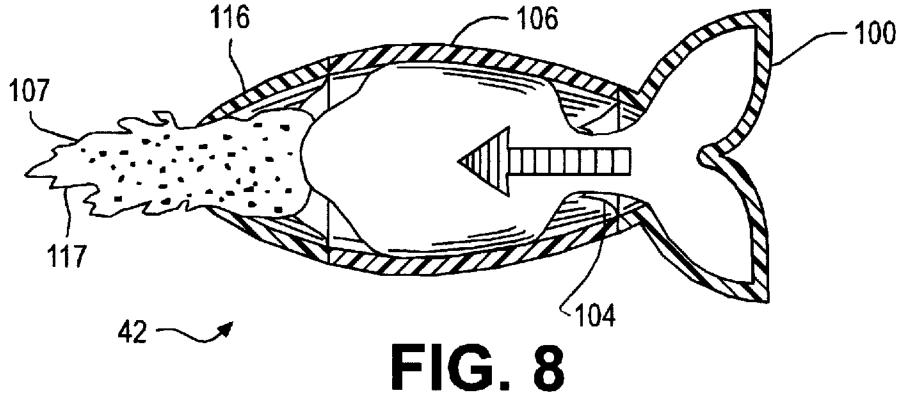
FIG. 8 is a cross-sectional view of the unit dose holder of FIG. 7 with its contents being expelled in response to the applied pressure.

An example of a unit dose holder 42 particularly suited to automatic rupture by the robotic apparatus of this invention is shown in FIGS. 6–8. The unit dose holder 42 is formed of three plastic parts. To readily convey the function of the unit dose holder, it may be formed to simulate a fish. The unit dose holder 42 has a pressurized gas container 100 corresponding in position to the fish's tail. The gas container 100 has a male threaded outlet 102 which is sealed with a readily ruptured membrane 104. The gas container 100 is formed of resilient plastic and is filled with pressurized, sterilized, and filtered air. The outlet 102 of the gas container 100 is threaded into engagement with a central medicament container 106 which corresponds in position to the fish's body. The central container 106 has a female threaded inlet 108 and a male threaded outlet 110, each of which are sealed with readily ruptured membranes 112. The central container 106 is filled with concentrated medicinal solutions 107 and is threadedly engaged with the female threaded inlet 114 of a discharge container 116. The discharge container 116 corresponds in position to the head of the fish. The discharge container 116 may be filled with medicinal powder 117, and has a weakened line of plastic 118 which corresponds in position to the fish's mouth. The weakened line of plastic 118 is easily ruptured in response to internal pressure within the unit dose holder. The threaded inlet of the discharge container is sealed with a readily ruptured membrane 120. When pressure is applied externally to the gas container 100, as shown in FIG. 7, the membranes 104, 112 are ruptured, and the gas enters the central container 106, applying pressure to the contents which in turns ruptures the membranes 120, 112 between the central container 106 and the discharge container 116. The result is to burst the line of weakened plastic 118 and expel the entire liquid and powder contents of the unit dose holder out from the unit dose holder, as shown in FIG. 8.

The robotic apparatus 20 thus fully controls the preparation of the administration bag without requiring manual processing. Not only can the apparatus thus rapidly make the necessary formulations, but it can be done with unwavering procedures which are not subject to human error. Furthermore, by the use of prefilled unit dose holders, variables with respect to precise quantities of liquids can be eliminated. A single pharmacist may thus oversee a large quantity of preparations. Moreover, because of the automatic nature of the apparatus 20, the pharmacist may be located remotely from the actual preparation site. For remote operation, the apparatus is outfitted with a radio receiver for receiving analog or digital signals, and a controller for receiving the signals and carrying out operations in response to those signals. This ability to remotely prepare solutions is particularly advantageous when it is costly or dangerous to have the pharmacist in close proximity to the patient. For example, a robotic apparatus 20 may be positioned on an orbiting space station, with the pharmacist operating the machine from earth. Or, as another example, a robotic apparatus in a combat field hospital may be operated by a pharmacist at the rear.

The mixing chamber also provides a valuable supervisory function, in that the exhausted unit dose holders may be preserved along with the used mixing chamber for several days after the final solution has been administered to the patient. Should any untoward symptoms develop in the patient, an accurate and verifiable record of the actual medicaments administered may be obtained by retrieving the mixing chambers used in the preparation of solutions for that particular patient, and examining the exhausted unit dose holders therein. There can then be no question of the actual components and quantities of medicaments which have been administered to the patient. If facilities for storage of the used mixing chambers are unavailable or too costly for particular application, a photographic or digital imaging record may easily be preserved by making an exposure of the mixing bag after preparation of the solution, and storing the image in a mechanically or electronically retrievable form. The unit dose holders may be formed with different markers, indicia, or coloring, to facilitate their identification in the record images. As a further check on the medicament contents, if sufficient computer processing capacity is available, conventional computer vision systems capable of discerning the different shapes and indicia of the unit dose holders may be employed which can identify and record the unit dose holders present in a particular mixing bag. Alternatively, bar code markings may be placed on the unit dose holders for reading by a laser scanner. The unit dose holders may be filled and quality checked by the manufacturer, where there can be certainty of successful inclusion of the proper dose in each holder.

Figure 5:
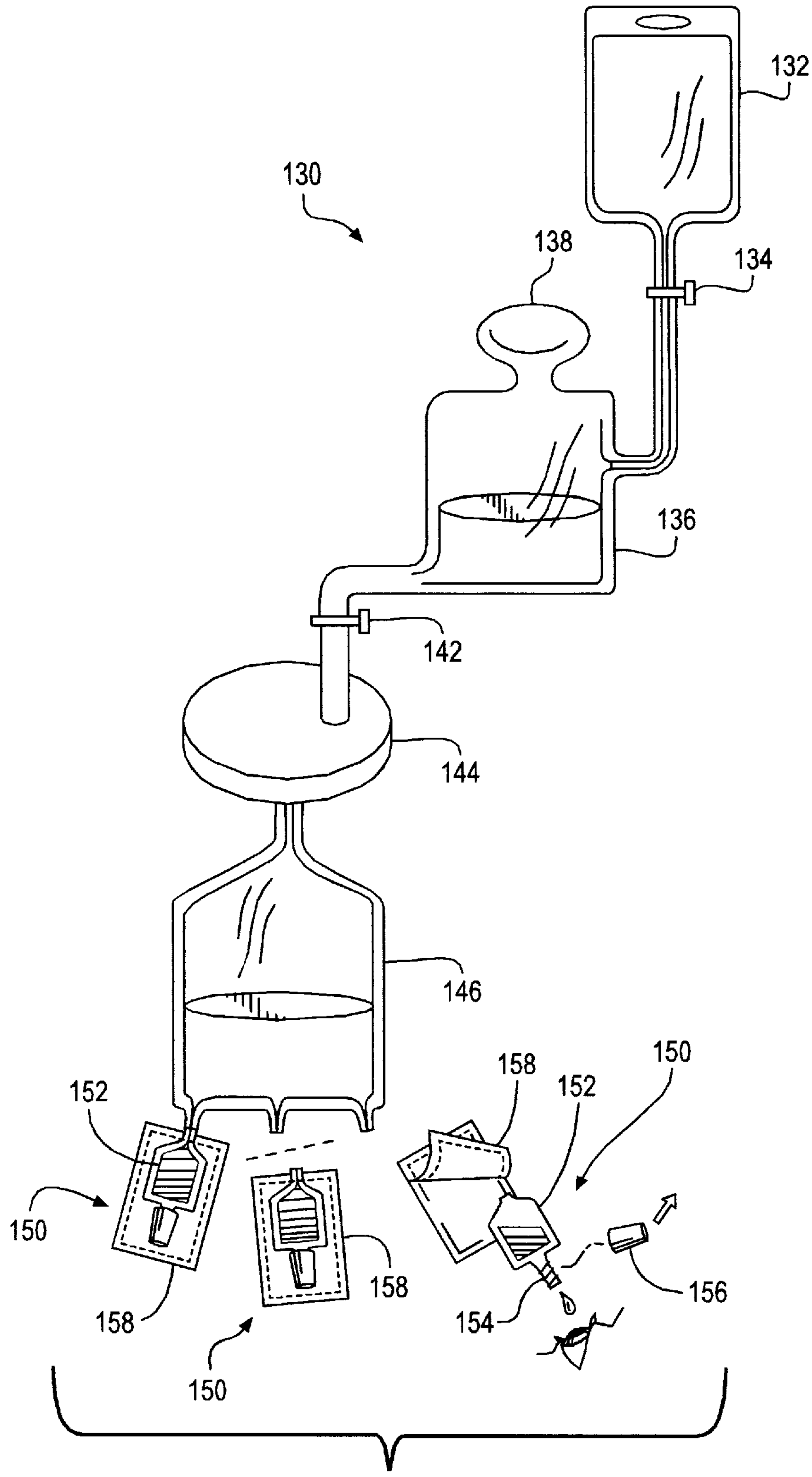
FIG. 5 is schematic view of an alternative embodiment apparatus of this invention for the preparation of ophthalmic unit doses of medicament solutions.

In addition to preparing solutions for intravenous administration, the assembly of this invention may be used to prepare individual unit dose ophthalmic solutions for application to a patient's eye, as shown in FIG. 5. The assembly 130 is similar to the assembly 22 in that it has a transparent plastic supply bag 132 prefilled with U.S.P. water and connected with a first valve 134 to a mixing bag 136. The mixing bag has an inlet 138 through which unit dose containers are introduced into a mixing chamber 138. A magnetic mixing bar 32 is disposed within the mixing bag. The mixing bag 136 is connected by a second valve 142 through a filter 144 to a pre-administration bag 146. The adding of the water and the unit dose holders 42 and the mixing and filtering of the solution is carried out just as described above. However, a plurality of ophthalmic solution containers 150 are formed to extend downwardly from the pre-administration bag 146. Each container 150 has a body 152 which holds the prescribed quantity of ophthalmic solution for a single dose, and a threaded dropper nozzle 154 which is capped with a pre-sterilized cap 156. Each container 150 and cap 156 are heat sealed within a removable plastic envelope 158. Once the solution has been drawn into the pre-administration bag 146, negative pressure is applied to the containers 150, to draw solution into the bodies 152 of the containers. Once full, a container 150 is heat sealed and severed from the pre-administration bag 146. The container 150 is then ready for later administration to a patient's eye 160 after removal of the cap 156 and the envelope 158.

It should be noted that unit dose holders of various different geometries and construction may be employed with this invention. Furthermore, the mechanism for manipulating the bags and for disposing dose holders and solution therein may be of various designs to accommodate the particular throughput and location needs of a particular application. In addition, the control of the process steps may be through any acceptable control means, such as a digital computer, a system of relays, etc.

Figure 9:
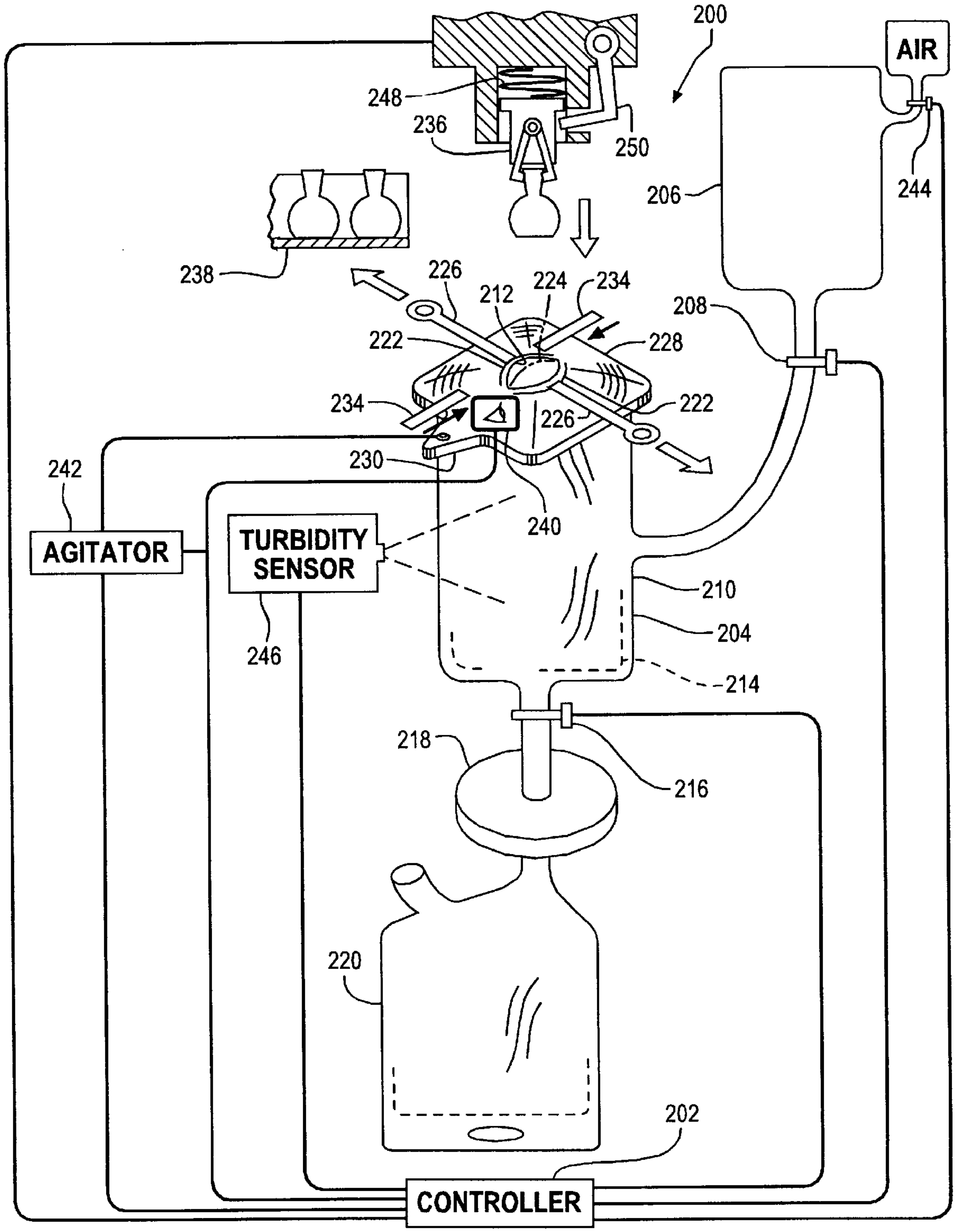
FIG. 9 is an isometric schematic view of an alternative embodiment apparatus of this invention, particularly adapted for low or microgravity environments.

In the absence of appreciable gravitational forces, for example aboard orbiting space stations or space vehicles, the apparatus of this invention may be modified to operate independently of gravity, as shown in FIG. 9. The apparatus 200 has a number of linkages and pressure applying structures which operate at the direction of an automated controller 202.

The preparation assembly 204, as shown in FIG. 9, has three connected bags, similar to the preparation assembly 22 discussed above. The preparation assemblies 204 are stored in a magazine for immediate access by the mechanism 200. Each preparation assembly has three connected bags in which the solution is prepared and contained. A transparent plastic supply bag 206 is prefilled and stored with U.S.P. water. The supply bag 206 is connected through a first check valve 208 to a mixing bag 210. The mixing bag 210 is transparent plastic and has an inlet 212 through which unit dose containers are introduced into a mixing chamber 214. The mixing bag 210 is connected by a second check valve 216 through a filter 218 to an administration bag 220. The inlet 212 is formed of two resilient flaps 222 which are molded as portions of the mixing bag 210 with a central slit 224 where the two flaps 222 come together. The natural resilience of the flaps causes the inlet 212 to remain in a closed position unless an external force is applied. The inlet 212 is opened by forces applied to two opposed opening links 226. The opening links 226 may be pin-connected to molded portions of the flaps 222, but are preferably heat welded to the flaps 222. The links are operated by the controller 202 to draw open the flaps 222 to admit a unit dose holder 42. The flaps 222 are formed in a generally stiff plastic cap portion 228 of the otherwise flexible mixing bag 210, which has an ear 230 which extends outwardly from the cap portion. The rigid ear 230 provides a location for gripping the entire preparation assembly 204, both for moving it from the storage magazine, not shown, and for positioning the links 226 in conjunction with reciprocating opening pins, not shown, and dose holder striking pins 234.

Once the prescription has been conveyed to the controller 202, typically by a pharmacist on Earth through radioed instructions, the controller causes a preparation assembly 204 to be gripped by the ear 230 and extracted from the magazine. The gripped assembly 204 is then brought into position such that the opening pins 232 engage the opening links 226. In so locating the preparation assembly 204, the central slit 224 is positioned below the unit dose dispensing arm 236. The arm 236 has a clamp thereon for grasping and extracting a unit dose holder 42 from a shelf 238, where the controller has deposited it. The arm 236 is manipulated by the controller to urge the unit dose holder toward the bag inlet 212. The unit dose holder may have an acceleration toward the inlet imparted to it by a spring 248 with a pawl release 250, a pneumatic ejection, a mechanical linkage, or other means. The opening links 226 are operated in concert with the movement of the arm 236 to allow the unit dose holder 42 to pass into the mixing chamber 214. Prior to the passage of the unit dose holder fully into the mixing chamber, the arm 236 is released. The force applied to the unit dose holder will cause it to continue on its path into the mixing chamber. An electric eye 240 detects the presence of the unit dose holder 42 at the opening and passes this information to the controller 202 which causes the striking pins 234 to drive toward one another and impact the pressurized gas container 100 of the unit dose holder. This impact causes the unit dose holder 42 to expel its contents within the mixing chamber as it moves fully within the mixing chamber and as the opening links are released to close the flaps 222 over the inlet 212.

Once all unit dose holders 42 necessary to the prescription have been discharged into the mixing chamber 214, sterile water or saline solution contained in pre-measured dispensing units in the supply bag 206 is introduced into the mixing chamber. The supply bag 206 has a positive expulsion bladder similar to that employed in a zero gravity fuel tank. Alternatively, devices also used in zero gravity fuel tanks, employing surface tension to separate fluids from air may also be employed. The valve 208 between the supply bag and the mixing bag is activated by the controller to allow the fluid to flow into the mixing chamber. The fluid may be caused to flow by the activation by a robot or squib of a valve 244 to inject a pre-determined quantity of air into the supply bag 206, where the air expands again a membrane or the surface of the fluid, causing it to flow through the check valve 208 into the mixing container.

Once the requisite pharmaceuticals and fluid are present in the mixing chamber 214, an agitator 242 is engaged with the ear 230 and activated to agitate the mixing bag 210. The agitator has a vibrating arm driven by a rotary electric motor or a piezoelectric motor which causes agitation until the mixture is uniformly mixed.

The mixing bag 210 incorporates transparent portions on which a turbidity sensor 246 can be mounted to monitor the progress of dissolution of the pharmaceutical suspension. A similar sensor monitoring optical index of refraction can be used to determine complete mixing of dissolved pharmaceuticals, as it will be observed when the solution is evenly mixed that the index of refraction of the liquid contained in the mixing bag will be uniform.

Once the solution has been fully mixed, the second check valve 216 between the mixing bag and the filter 218 is opened, and a vacuum jacket is placed around the administration bag 220 and the reduced pressure on the bag 220 draws the solutions in the mixing chamber into the administration bag through the cold sterilization filter 218.

The unit dose containers remain within or attached to the mixing container serving as a positive record of what pharmaceuticals have been added to the intravenous solution.

Once the solution has been drawn into the administration, the apparatus 20 may automatically heat seal and cut the administration bag from the remainder of the preparation assembly 204 for delivery to the patient.

The apparatus of this invention is preferably used in conjunction with a control program which double checks any prescriptions entered by the operating pharmacist. This control program may contain an index of rules for combining pharmaceuticals which will prevent the preparation of a solution which could be harmful to the patient. There are many compositions which, although not harmful alone, are incompatible with other pharmaceuticals. Because a solution is prepared by the apparatus of this invention only once all unit doses have been selected, it is possible for the controller to prevent incompatible compounds from being commingled in a solution and thereby avoid administering them to a patient.

It should be noted that various other mechanisms for introducing the unit doses of pharmaceuticals into the mixing chamber can be employed. For example, the mixing bag may be formed with a plurality of unit does admission ports, comprised of a snap or bayonet fitting with a check valve thereon, into which unit does holders may be connected. Once attached, the unit dose holders cannot be removed, thus serving as a record of what pharmaceuticals have been added to the bag. The unit dose holders can also be formed in such a way that a mechanical piston can eject the contents into the mixing bag, or so they may be connected to a source of compressed air through a hose or the like to eject the contents into the mixing chamber on command. In addition, rather than applying negative pressure to the administration bag, positive pressure may be applied to the mixing bag. The agitation of the mixing bag may by produced by a chaotic mechanical system to produce optimal mixing in zero gravity conditions.

It is understood that the invention is not limited to the particular construction and arrangement of parts herein illustrated and described, but embraces such modified forms thereof as come within the scope of the following claims.

I claim:

1. A method for remotely preparing solutions for administration to humans comprising the steps of:

extracting a mixing bag from a store of mixing bags;

introducing a container of a predetermined amount of a medicament into the mixing bag in response to a remotely transmitted signal;

introducing water into the mixing bag from an attached liquid supply bag;

breaking the container to eject the medicament into the mixing bag;

mixing the water and the medicament to form a solution; and detecting the degree of mixing of the medicament and the water by a sensor positioned exterior to the mixing bag;

after a desired level of mixture has been obtained as detected by the sensor, applying negative pressure to a second bag connected to the mixing bag through a filter to draw a filtered solution into the second bag.

2. The method of claim 1 further comprising the steps of:

transmitting a radio signal containing instructions as to which solution to prepare; and receiving the transmitted signal at a location remote from the location from which it was transmitted, and performing the steps of claim 1 in response to the instructions.

3. The method of claim 1 wherein the step of introducing water into the mixing bag comprises actuating a valve interposed between the supply bag and the mixing bag and applying pressure to the supply bag.

4. The method of claim 1 wherein the means for drawing the solution from the mixing bag comprises a negative pressure chamber enclosing the administration bag.

5. The method of claim 1 wherein the step of breaking the container comprises rupturing the container prior to its introduction into the mixing bag.

6. The method of claim 1 wherein the step of breaking the container comprises engaging the container within the bag to rupture the container and discharge the contents therefrom.

7. The method of claim 1 further comprising the steps of:

preserving the mixing chamber and broken container after administration of the solution to a patient;

reviewing the contents of the mixing chamber at a time subsequent to the preparation of the solution to verify the contents of the solution administered to the patient.

8. The method of claim 1 further comprising the step of visually identifying the contents of the mixing chamber after the preparation of the solution to determine the contents of the solution.

9. The method of claim 1 wherein the mixing step further comprises engaging a portion of the mixing bag and mechanically agitating it.

10. A method for remotely preparing solutions for administration to humans comprising the steps of:

extracting a mixing bag from a store of mixing bags;

introducing a container of a predetermined amount of a medicament into the mixing bag in response to a remotely transmitted signal;

introducing water into the mixing bag from an attached liquid supply bag;

breaking the container to eject the medicament into the mixing bag;

mixing the water and the medicament to form a solution;

applying negative pressure to a second bag connected to the mixing bag through a filter to draw a filtered solution into the second bag; and detecting the signals from an electric eye positioned to view the mixing bag, and halting the introduction of water into the mixing bag when the level detected by the electric eye satisfies a predetermined value.

11. A method for remotely preparing solutions for administration to humans comprising the steps of:

extracting a mixing bag from a store of mixing bags;

introducing a container of a predetermined amount of a medicament into the mixing bag in response to a remotely transmitted signal;

introducing water into the mixing bag from an attached liquid supply bag;

breaking the container to eject the medicament into the mixing bag;

mixing the water and the medicament to form a solution; and applying negative pressure to a second bag connected to the mixing bag through a filter to draw a filtered solution into the second bag; wherein the mixing step comprises agitating a ferromagnetic metal bar positioned within the mixing bag by rotating a magnetic element exterior to the mixing bag.

* * * * *